United States Patent [19]
Green et al.

[11] Patent Number: 5,807,327
[45] Date of Patent: Sep. 15, 1998

[54] CATHETER ASSEMBLY

[75] Inventors: Nicholas A. Green, Kinnelon; Robert W. Reinhardt, Chatham, both of N.J.

[73] Assignee: Ethicon, Inc., Somerville, N.J.

[21] Appl. No.: 569,825

[22] Filed: Dec. 8, 1995

[51] Int. Cl.⁶ .................................................. A61M 29/00
[52] U.S. Cl. ............................................. 604/96; 694/194
[58] Field of Search ............................. 604/96, 101, 104, 604/264, 265; 606/191–195

[56] References Cited

U.S. PATENT DOCUMENTS

| | | | |
|---|---|---|---|
| 5,102,417 | 4/1992 | Palmaz | 606/195 |
| 5,195,984 | 3/1993 | Schatz | 606/195 |
| 5,290,306 | 3/1994 | Trotta et al. | 604/96 |
| 5,344,401 | 9/1994 | Radisch et al. | 604/96 |
| 5,358,486 | 10/1994 | Saab | 606/194 X |

*Primary Examiner*—John D. Yasko
*Attorney, Agent, or Firm*—Paul A. Coletti

[57] ABSTRACT

A stent delivery system including a stent delivery catheter, a stent dilatation balloon sealingly affixed to the catheter and adapted for inflation by a pressurized fluid introduced into the catheter, and an expandable stent surrounding the balloon and adapted for implantation into a bodily vessel upon inflation of the balloon. The system also includes structure integral with the balloon and possibly the catheter for resisting movement of the stent relative to the balloon throughout all phases of a stent delivery and implantation operation prior to deflation and withdrawal of the balloon from the stent following implantation of the stent.

21 Claims, 7 Drawing Sheets

CATHETER ASSEMBLY

The present invention relates in general to surgical systems and, more particularly, to catheter assemblies having an inflatable balloon and a stent adapted for implantation in a bodily vessel.

BACKGROUND OF THE INVENTION

The use of balloon catheters for high pressure dilation of occluded bodily vessels such as arteries and the like is commonplace. Balloon coronary angioplasty, for example, is used throughout the world as an alternative to open-heart coronary bypass surgery. This surgical technique typically involves routing a dilatation catheter having an inflatable expander member (balloon) on the distal end thereof through the vascular system to a location within- a coronary artery containing a stenotic lesion. The expander member is then positioned so as to span the lesion. A fluid is introduced into the proximal end of the catheter to inflate the expander member to a predetermined elevated pressure whereby the lesion is compressed into the vessel wall restoring patency to the previously occluded vessel. The expander member is then deflated and the catheter is removed.

A disadvantage of balloon angioplasty, however, is that it occasionally results in short or long term failure. That is, vessels may abruptly close shortly after the procedure or gradual restenosis may occur up to several months thereafter.

To counter the tendency of recurrent vessel occlusion following balloon angioplasty, implantable endoluminal prostheses, commonly referred to as grafts or stents, emerged as a means by which to achieve long term vessel patency. Stated simply, a stent functions as permanent scaffolding to structurally support the vessel wall and thereby maintain coronary luminal patency.

In a typical procedure, stent implantation immediately follows a balloon angioplasty. In order to accommodate presently available stent delivery systems, angioplastic dilatation of the lesion must) produce a residual lumen large enough to accept a stent-carrying balloon dilation catheter and a delivery sheath which surrounds the catheter and passes through an exterior guide catheter. In this regard, the apparatus and methods deployed in placing an arterial stent are in many respects similar to those used in an angioplasty procedure.

Following angioplasty, the guide catheter remains in position and the angioplasty catheter and its deflated balloon are withdrawn and discarded. Thereafter, a stent delivery system is routed through the guide catheter to a position whereat its distal end is disposed substantially coextensive with the distal end of the guide catheter and immediately proximate, i.e., upstream, of the previously expanded lesion.

The stent delivery system normally comprises a stent premounted, such as by crimping, onto the folded stent dilatation balloon at the distal end of a stent delivery catheter. Conventional stents may vary in length from about 5 to about 100 mm depending upon the intended intraluminal application, e.g., the aorta or the coronary, iliac, femoral renal, subclavian and other arteries, with the expansion balloon typically being somewhat larger than its corresponding stent. The stent, which is generally fabricated from expandable stainless steel lattice or mesh of about 0.0025 to about 0.005 inches wall thickness, is normally formed as a substantially cylindrical member having an inner diameter of from about 2.5 to 5.0 mm (unexpanded) which may be expanded to an inner diameter of from about 3 to about 30 mm as determined by the diameter of the expansion balloon when inflated. The stent expansion balloon may be formed of polyethylene) or other suitable material. The stent delivery system additionally comprises the aforementioned stent catheter delivery sheath or, more simply, the "delivery sheath" that envelops the balloon, stent and delivery catheter and extends substantially the entire length of the delivery catheter.

Once properly positioned relative to the guide catheter, the stent delivery system is extended from the distal end of the guide catheter until the stent spans the previously expanded lesion. Thereafter, the delivery sheath, which is slideable relative to the delivery catheter, balloon and stent, is withdrawn into the guide catheter to expose the balloon and stent. The delivery catheter is then supplied with a pressurized fluid. The fluid expands the balloon and the associated stent to a desired diameter sufficient to exceed the elastic limit of the stent whereby the stent becomes imbedded in and permanently supports the vessel wall. The balloon is then deflated and it, the stent catheter and guide catheter are withdrawn, leaving the expanded stent and an open lumen.

A troublesome disadvantage of currently available balloon-expandable stent assemblies is retention of the stent on the balloon throughout the relevant stent placement procedure, particularly during withdrawal of the delivery sheath prior to implantation, and especially if sheath withdrawal is coupled with subsequent shifting of the stent delivery catheter. With existing designs, the stent has been occasionally known to positionally slip along the balloon during negotiation of the anatomy and/or inflation of the balloon. Even under the best of circumstances when the misaligned stent has not yet been deployed and can be successfully retrieved, the stent delivery system usually must be withdrawn and the procedure repeated using a new assembly. Alternatively, the stent may be disposed so as to partially span or possibly fail to span any portion of the target lesion, in which case a supplemental stent placement would be required. In the worst case, a stent may substantially or perhaps completely slip along the length of the balloon prior to balloon inflation.

Stent slippage cannot be overcome by simply increasing the crimping force applied when mounting the stent to the folded dilatation balloon. Increased crimping force may result in overcrimping of the stent. overcrimping may damage the stent, and therefore hinder its proper expansion and implantation, and possibly puncture the balloon.

Many commercially available stent delivery systems, as well as those disclosed in U.S. Pat. Nos. 4,733,665, 4,739,762, 4,776,337, 5,102,417 and 5,195,984 utilize a delivery sheath over the delivery catheter as a nondestructive means by which to maintain the position of the stent relative to the balloon during stent delivery. The delivery sheath is intended to restrict movement of the stent relative to the balloon as the stent delivery catheter is routed through the body. Additionally, the delivery sheath is designed to constrain stent shifting, as well as eliminate snagging of the stent against the vessel walls and any attendant damage to the vessel walls, when moving the catheter through the body to the designated implantation site. However, the delivery sheath does not always prevent stent shifting, especially when the sheath is withdrawn into the guide catheter. And, once exposed, the unguarded end edges of the stent are capable of snagging the surrounding bodily vessel.

The aforementioned patent documents also describe additional means in the form a recessed seat formation provided on the exterior of the delivery catheter which may complement the delivery sheath's ability to retain the stent on the balloon. Such means, which have not been commercially embraced, required the delivery catheter to be thickened in the regions bounding the seat formation, which increases the cross-sectional profile of the catheter and the delivery system in general.

Other inherent disadvantages of existing stent delivery systems include the added stiffness and increased diameter that the sheath imparts to the stent delivery system. Increased stiffness and diameter results in decreased system performance in terms of trackability, profile, negotiation of tight lesions and/or tortuous anatomy and may prevent the stent from being deployed in locations that are difficult to reach. Moreover, larger introducer sheaths and guide catheters must be used to accommodate such systems, thus increasing the likelihood of bleeding complications.

An advantage exists, therefore, for a stent delivery system which assumes a smaller cross-sectional profile than similar systems currently known in the art. A further advantage exists for a stent delivery system which assures positive retention of the stent relative to the stent expansion balloon throughout all phases of the stent delivery and implantation operation prior to deflation and withdrawal of the balloon from the implanted stent.

SUMMARY OF THE INVENTION

The present invention provides a stent delivery system including a stent delivery catheter, an inflatable balloon at the distal end of the stent delivery catheter and a stent carried by the balloon. Prior to inflation the balloon is folded into a compact substantially cylindrical profile operable to support the stent for delivery of same to a desired implantation site within a bodily vessel. When the stent is properly disposed relative to the implantation site the balloon is inflated thereby radially expanding and implanting the stent into the vessel. The stent delivery system further includes stent retention means integral with the stent dilatation balloon for positively retaining the stent on the balloon throughout all phases of the stent delivery and implantation operation prior to deflation and withdrawal of the balloon from the expanded stent.

The stent retention means may be realized in several manifestations associated with the stent dilation balloon or a combination of the balloon and the stent delivery catheter. According to a presently contemplated embodiment the stent retention means may comprise a coating having a relatively high coefficient of friction applied to at least a portion of the exterior surface of the balloon underlying the stent. To the extent the high coefficient of friction material may be present on the balloon, it is also preferable that such material be additionally provided with a layer of material operable to reduce the affinities of the layer of high coefficient of friction material for itself and the outer guide catheter to facilitate passage of the stent delivery system through the outer guide catheter and to promote unrestricted expansion of the balloon.

To further enhance stent retention, the stent delivery catheter may be comprised of inner and outer coaxially disposed tubular members defining a balloon inflation fluid passageway therebetween wherein the inner tubular member may be provided with a reduced diameter portion having radially outwardly projecting opposite ends. The reduced diameter portion and the relatively enlarged opposite ends of the stent delivery catheter inner member thus define a recessed saddle or seat formation. When the balloon is folded about the seat formation, and the stent is crimped about the folded balloon, the balloon generally conforms to the contours of the recessed seat formation. That is, at least the central portion of the balloon is compressed into the reduced diameter portion of the stent delivery catheter inner member by the crimped stent. Additionally, if the balloon is longer than the stent and seat function the exposed opposite ends of the balloon will be undergirded and, therefore, urged relatively radially outwardly by the enlarged opposite ends of the seat formation to define somewhat enlarged stop means which further resist axial movement of the stent relative to the balloon during delivery and placement of the stent. Moreover, although enlarged relative to the reduced diameter central portion, the opposite ends of the seat formation of the stent delivery catheter inner member are preferably constructed so as not to exceed the dimensions of presently existing inner members of such catheters. In that way, the cross-sectional profile presented by the delivery catheter, folded balloon and stent is no greater than that provided by their counterparts in currently available stent delivery systems.

Apart from enhanced stent retention, by being integral with the inflatable stent dilatation balloon, the stent retention means of the present invention eliminates the need for the delivery sheath required by may commercially available stent delivery systems. By disposing of such component, the present invention offers a stent delivery system of lesser cross-sectional profile and greater structural flexibility than heretofore achievable. As such, the present system is capable of negotiating tight lesions and tortuous anatomy with less difficulty than existing systems. It also requires a smaller introducer sheath and guide catheter and thereby reduces the possibility of bleeding complications.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein.

DETAILED DESCRIPTION OF THE INVENTION

Since they do not form part of the present invention, balloon angioplasty methods and apparatus will not be described in detail. However, as it will provide a greater appreciation of the equipment and procedures common to both balloon angioplasty and stent implantation, the following is a brief summary of a typical balloon angioplasty procedure. As described, the procedure is one in which a coronary artery lesion may be dilated, although the essential steps and equipment used in the operation are generally similar to those involved in most angioplastic lesion dilatations. For example, by selecting the appropriate vascular point of entry and properly dimensioned angioplasty catheter and peripheral equipment, the technique may be adapted to perform luminal enlargement of the iliac, femoral, subclavian, renal carotid and other arteries, as well as the aorta and other bodily vessels.

Local anesthesia is administered and the femoral artery is entered with a puncture needle. A guide wire is introduced into the femoral artery through the puncture needle. The needle is removed and an introducer sheath is introduced and advanced over the guide wire into the femoral artery. The introducer sheath is usually several centimeters in length and up to about 10 F outer diameter for coronary applications, where 1 F (French or Fr) ≈0.013 in.≈0.333 mm. Contrast media is then injected through the catheter to confirm the intraluminal position. An open-ended guide catheter is then introduced through the introducer sheath. The guide catheter is advanced over the guide wire and into the proximal aorta until it becomes seated in the coronary ostium.

An angioplasty balloon catheter is then selected to correspond, when dilated, to the diameter of the coronary artery proximal the lesion. The balloon catheter is inserted through the introducer sheath and routed through the guide catheter and coronary arteries until the folded balloon at the distal end of the catheter spans the lesion. A pressurized fluid is then introduced into the proximal end of the catheter which expends the balloon and dilates the lesion. Thereafter, the balloon is deflated and the angioplasty balloon catheter is withdrawn. If the angioplasty is successful the coronary artery should appear substantially similar to the lower left branch of the blood vessel system depicted in FIG. 1A.

Figure 1A:
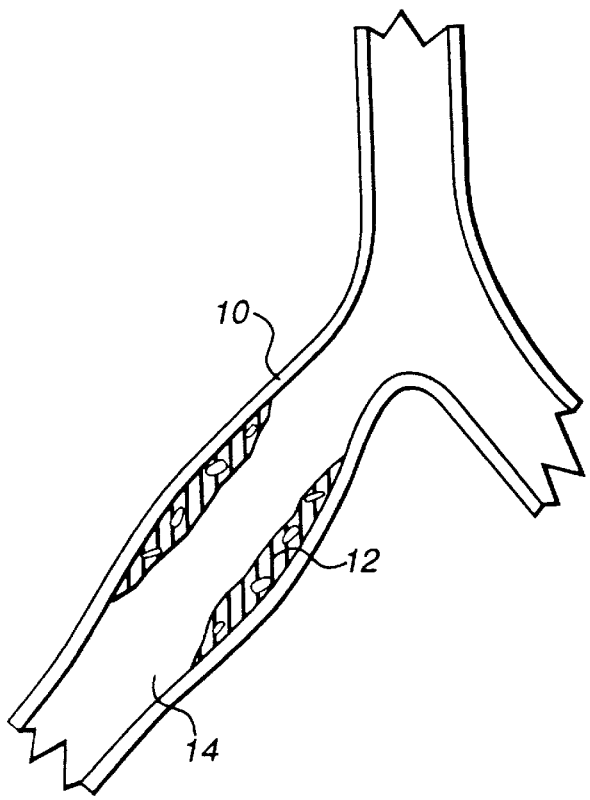
FIG. 1A is a longitudinal cross-section view of a blood vessel immediately following a technically successful balloon angioplasty.

Referring to FIG. 1A, there is shown a longitudinal cross-section of a blood vessel 10, e.g., a coronary or other artery, immediately following a balloon angioplasty. As is typical of such a procedure, a lesion 12, which may be either a de novo or restenotic occlusion, is dilated by an expandable angioplasty balloon to enlarge the lumen 14 of vessel 10 across the lesion. Following angioplasty, the ability to cross a dilated lesion such as lesion 12 with both a guide wire and a stent-carrying balloon dilatation catheter is necessary to perform stent placement. Moreover, using conventional stent delivery systems, the dilated lumen across lesion 12 must also be sufficiently expanded to accommodate a stent catheter delivery sheath, discussed below, which surrounds the balloon catheter and stent.

Figure 1B:
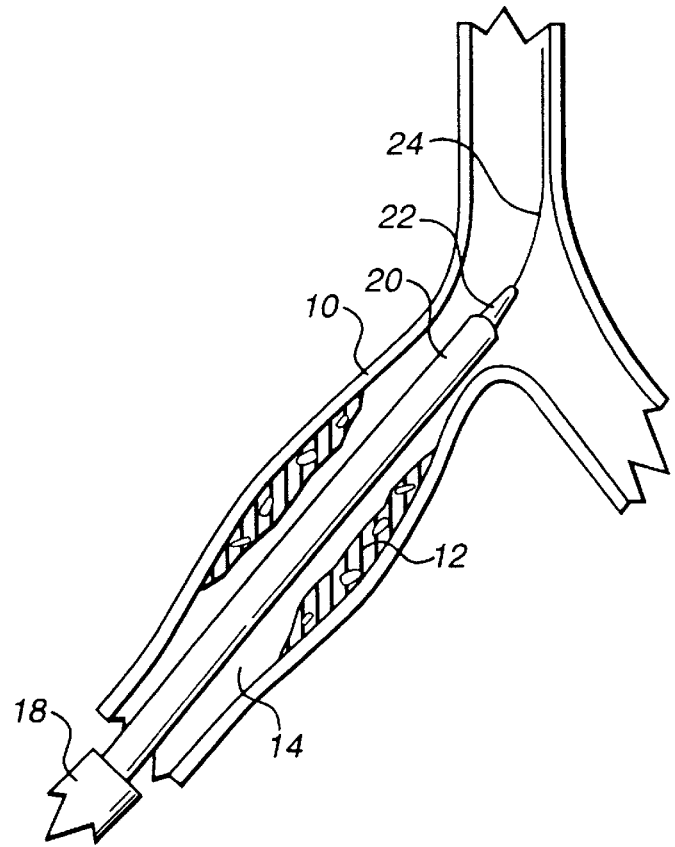
FIGS. 1B through 1E are sequential views of a stent implantation procedure using a conventional stent delivery system.

FIGS. 1B through 1E depict in sequential fashion the delivery and implantation of a stent across lesion 12 using a conventional stent delivery system of the type known as the Palmaz-Schatz™ balloon-expandable stent delivery system manufactured by Johnson & Johnson Interventional Systems Co. of Warren, N.J. Turning initially to FIG. 1B, a guide catheter 18 is inserted through an unillustrated introducer sheath and routed through the vascular system until its distal end is disposed, as generally shown, proximate the dilated lesion 12. The guide catheter 18 may be fabricated from a variety of suitable materials. A typical construction, comprises an elongated flexible body formed from stainless steel braid covered with a nylon jacket and internally lined with polytetrafluoroethylene (PTFE) or other suitable lubricious material to facilitate passage of the stent delivery system therethrough. As a protective measure, the distal end of the guide catheter is provided with a tip having a rounded leading opening to minimize friction and/or snagging of the guide catheter as it traverses the patient's vasculature. The tip is commonly formed of a low durometer urethane or similar material capable of ready molding into a smoothly contoured outer profile corresponding in diameter to the remainder of the guide catheter.

Currently existing stent delivery systems typically include a stent catheter delivery sheath ("delivery sheath") 20. Delivery sheath 20 surrounds and is slideable relative to the other components of the stent delivery system which are discussed in greater detail in connection with the descriptions of FIGS. 1C and 1D. In existing designs, the guide catheter must have a lumen size suitable to accommodate the introduction of a 5 F to 7 F stent delivery system (including delivery sheath 20) This requires a guide catheter size of at least 8 F. The stent delivery system including the delivery sheath 20 is first routed through the guide catheter 18 to a position where its distal end is disposed substantially coextensive with the distal and of the guide catheter and immediately proximate the previously dilated lesion 12. From there the delivery sheath 20 is advanced either together with or, more preferably, independently of the remainder of the stent delivery system until it extends entirely across lesion 12 as depicted in FIG. 1B.

Conventional stent delivery systems also comprise a stent delivery catheter 22. The stent delivery catheter typically has a length between about 15 cm and 150 cm, and usually about 65 cm to 150 cm. The catheter is usually advanced over a thin (approximately 0.010 inches diameter) guide wire 24. The guide wire 24 may be the same or different than the guide wire used to advance the balloon angioplasty catheter. Guide wire 24 facilitates passage of the catheter 22 through delivery sheath 20 as well as gently direct the catheter, as may be necessary, through vasculature downstream of the distal end of the guide catheter 18 so as to minimize damage to either the stent delivery system or the bodily vessel's walls.

Figure 1C:
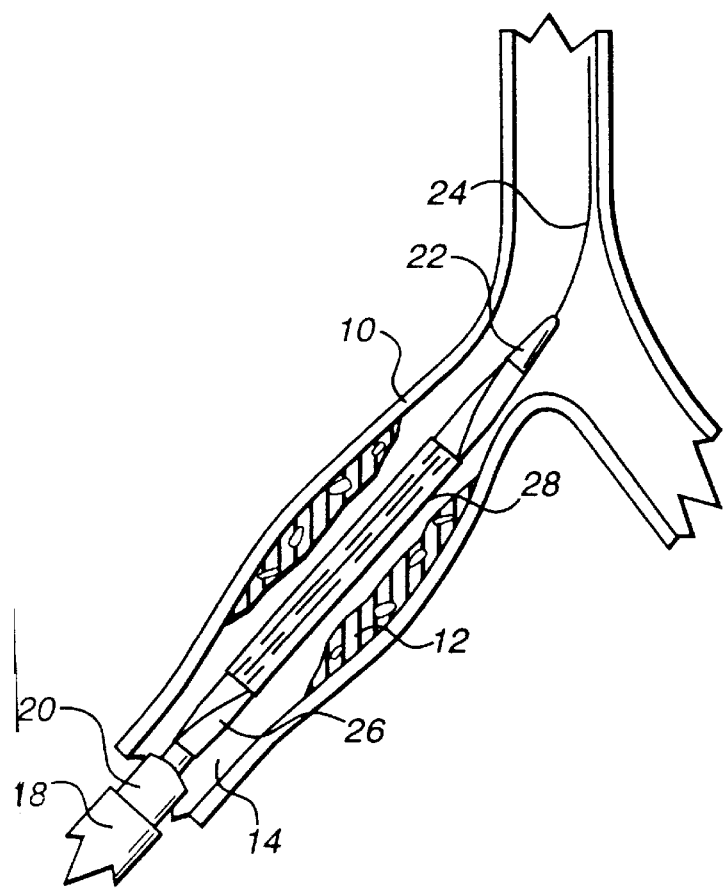

After the delivery sheath 20 and the stent delivery catheter 22 have been properly positioned across lesion 12, the delivery sheath is withdrawn into the guide catheter 18 as shown in FIG. 1C to expose the other essential components of the stent delivery system. Folded around and sealingly attached the distal end of the stent delivery catheter 22 is a stent expansion or dilatation balloon 26 typically fabricated from polyvinyl chloride (PVC), polyethylene, other suitable material. The walls of the balloon preferably have a thickness of between about 0.0002 and 0.004 inches.

Commercially available stent delivery systems also comprise a stent 28, such as the Palmaz-Schatz™ stent manufactured by Johnson & Johnson Interventional Systems Co. of Warren, N.J., which is premounted, such as by crimping, onto the folded stent dilatation balloon 26 at the distal end of the stent delivery catheter 22. The stent may vary in length depending upon its intended intraluminal application, although the length generally ranges from about 5 to about 100 mm, with the dilation balloon 26 normally being somewhat larger than its corresponding stent. The stent 28, which is generally fabricated from expandable stainless steel lattice or mesh of about 0.0025 to about 0.005 inches wall thickness, is normally formed as a substantially cylindrical member having an inner diameter of from about 2.5 to about 5.0 mm (unexpanded). Upon inflation of balloon 26, stent 28 may be dilated to an inner diameter of from about 3.0 to about 30.0 mm as determined by the diameter of the inflated dilatation balloon and the bodily vessel in which the stent is to be implanted, e.g., the aorta or the coronary, iliac, femoral renal, subclavian, carotid or other arteries.

Figure 1D:
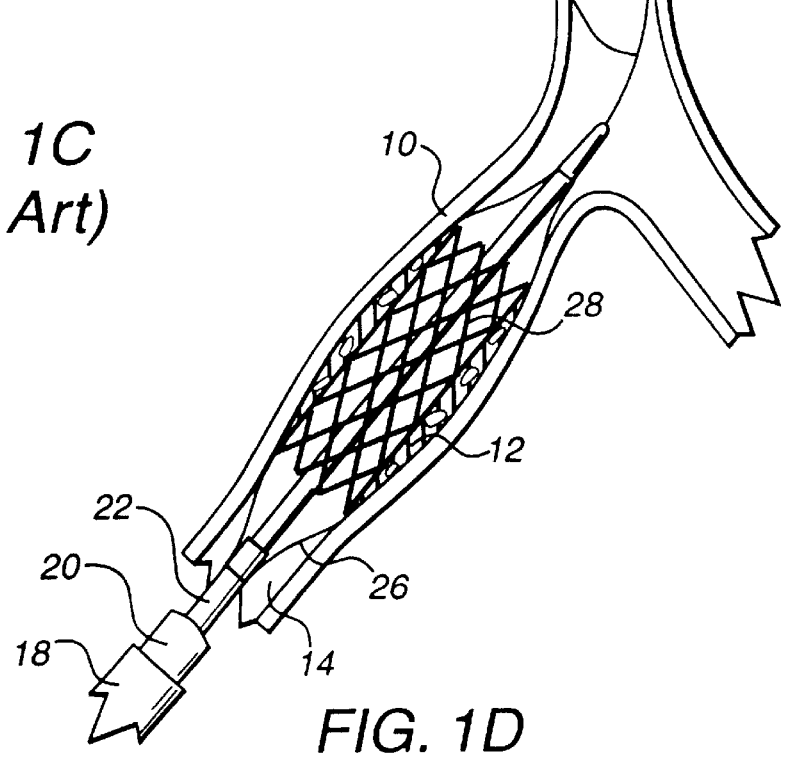
Figure 1E:
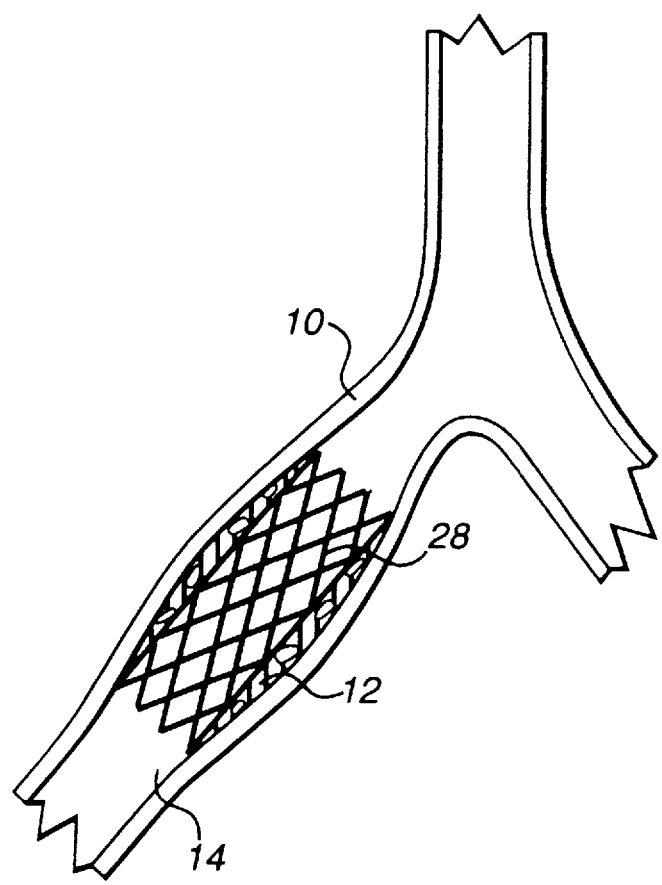

With the exposed stent 28 in a position spanning the lesion 12 as illustrated in FIG. 1C, the delivery catheter 22 is supplied with a pressurized fluid (either liquid or a compressed gas) which inflates the balloon 26 and thereby dilates the stent 28 to a desired diameter sufficient to radially outwardly impinge against and support the wall of vessel 10 in the manner shown in FIG. 1D. The balloon 26 is then deflated and it, the stent delivery catheter 22 and delivery sheath 20 are withdrawn, leaving the dilated stent 28 imbedded in the wall of vessel 10 and an open lumen 14 as reflected in FIG. 1E.

While generally effective, stent delivery systems of the sort thus far described, even with the provision of delivery sheath 20, cannot always prevent slippage of the stent 28 relative the balloon 26 as the delivery catheter 22 is routed through a patient's vasculature, and especially when the sheath is withdrawn into the guide catheter immediately prior to balloon inflation. Moreover, the very presence of the delivery sheath 20 imparts increased size and stiffness to the stent delivery system. This limits their viable application in patients having tortuous anatomy and/or narrow lesion lumens following balloon angioplasty.

The present invention proposes stent delivery systems in which the stent retention means are integral with at least one and possibly both of the stent dilatation balloon and stent delivery catheter. Stent delivery systems according to the invention obviate the need for a stent delivery sheath and reliably retain the stent on the balloon throughout all phases of stent delivery and implantation prior to deflation and withdrawal of the balloon from the implanted stent.

Figure 2:
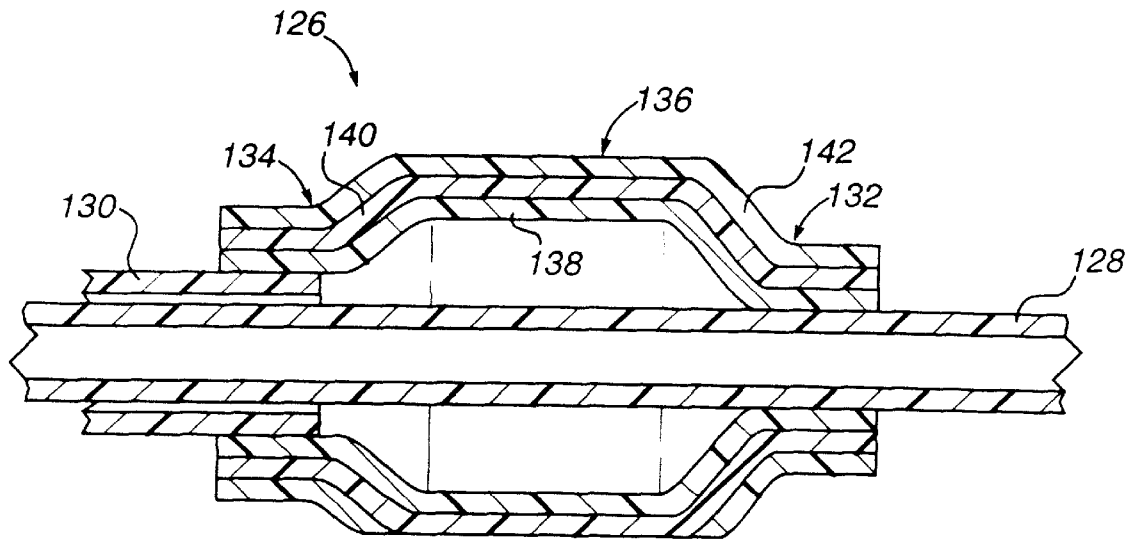
FIG. 2 is a longitudinal cross-sectional view of an inflated stent delivery balloon having stent retention means in accordance with a first preferred embodiment of the stent delivery system of the present invention.

A stent delivery balloon 126 having integral stent retention means in accordance with a first preferred embodiment of the stent delivery system of the present invention is shown in FIG. 2. The embodiments of the invention depicted in this figure and that shown in FIG. 3 may be successfully used in conjunction with conventional stents and delivery catheters such as the aforementioned stent delivery catheter 22 or the delivery catheter of the present invention illustrated in FIGS. 4A and 4B and discussed infra. Further, the balloon 126 is shown fully inflated to best display its structural features. It will be understood that balloon 126 is tightly folded around a stent delivery catheter and, until inflation, is maintained in that condition by a stent which is crimped thereabout in the manner known in the art.

Conventional stent delivery catheters such as catheter 22 typically comprise an inner tubular body member 128 and a coaxially disposed outer tubular body member 130. The guide wire 24 is typically threaded into the distal end of the inner tubular body member 128 to enable the catheter to be easily advanced along the guide wire to the desired treatment site. The inner and outer tubular members 128 and 130 may be formed of any plastic material having sufficient flexibility to negotiate potentially tortuously configured bodily vessels. The space between the coaxially disposed tubes 128,130 defines a passageway which allows for injection of the pressurized balloon inflation fluid.

Balloon 126 is comprised of first and second end portions 132 and 134 which may be fixedly and sealingly attached respectively to the inner and outer tubular body members 128, 130 of the stent delivery catheter 22 by adhesives, heat bonding, solvent bonding, or other suitable means. First and second end portions 132, 134 are contiguous with a substantially cylindrical central portion 136 which defines the "flat" or "working length" of the balloon about which the crimped stent resides prior to inflation and by which the stent is essentially uniformly dilated upon inflation. The balloon 126 may be manufactured to any length necessary and may be somewhat longer than the stent it is intended to dilate.

Balloon 126 may be formed from any of several manufacturing techniques known in the art. In the embodiment shown in FIG. 2, balloon 126 is comprised of a first inner layer 138 of tough but flexible plastic material having high tensile strength and burst resistance and low radial expansion (distensibility) beyond its formed diameter under high inflation pressures. Acceptable materials include, but are not limited to, copolymers such as ABS (acrylonitrile—butadiene—styrene), ABS/nylon, ABS/polyvinyl chloride (PVC), ABS/polycarbonate, and polyesters such as polyethylene, polyethylene terephthalate (PET), polybutylen terephthalate (PBT), polyethylene naphthalate (PEN), liquid crystal polymer (LCP), polyester/polycaprolactone and polyester/polyadipate, and polyethers such as polyetheretherketone (PEEK), polyethersulfone (PES), polyetherimide (PEI) and polyetherketone (PEK), as well as polyementhylpentene, polyphenylene ether, polyphenylene sulfide and styrene acrylonitrile (SAN).

Preferably, however, first layer 138 is formed from PET having a thickness of between about 0.0004 and 0.0012 inches. And, the inner layer 138 may be fabricated by known processes such as extrusion, blow molding, dipping, vacuum forming, and the like.

Balloon 126 further includes a second layer 140 disposed exteriorly of first layer 138 and comprised of a material having a comparatively high coefficient of friction relative to the inner layer. Nonexclusive examples of acceptable materials of which second layer 140 may be composed include thermoplastic elastomers, rubber, neoprene, latex and urethane compounds, especially polyurethane. Second layer 140 must therefore be capable of exerting relatively high shear forces against the inner cylindrical surface of a stent when the stent is crimped about the balloon to resist displacement of the stent relative to the balloon as the stent delivery system traverses the guide catheter and the patient's vasculature.

In this regard, second layer 140 is preferably formed from a suitable urethane having a thickness of about 0.0004 to 0.0006 inches. TABLE 1 reveals that such material necessitates, for a 15 mm stent having an inner diameter of 1.3 mm, the application of about 1.0 pound of shear force to cause slippage between the crimped stent and a folded urethane covered balloon. By contrast, TABLE 1 indicates that conventional stent delivery systems of comparable dimensions require no more than about 0.3 pounds of shear force to cause slippage between the crimped stent and folded balloon. Provision of the high coefficient of friction second layer 140 thus produces a several fold increase in stent retention capability in relation to currently available stent delivery systems such as depicted in FIGS. 1B through 1D. Further, although having a high coefficient of friction, experimentation has shown that the second layer 140 does not exhibit appreciably greater adhesion to the inner surface of the stent following dilation than currently existing stent dilatation balloons. Accordingly, the deflated balloon 126 including first layer 138 and second layer 140 has been found to be readily withdrawn from an implanted stent with little tendency to adhere to the stent. An additional benefit of the second layer 140 is that it increases the balloon's resistance to pinholes and premature rupture due to possible overcrimping of the stent.

TABLE 1

| STENT* | | BALLOON | | STENT |
|---|---|---|---|---|
| Length (mm) | Inner Diameter (mm) (unexpanded) | Length (mm) | Composition | SLIPPAGE FORCE (lbs.) |
| 15 | 1.3 | 16 | Polyethylene | 0.3 |
| 15 | 1.3 | 16 | PET with urethane Coating | 1.05 |

*Stents are Palmaz-Schatz ™ balloon-expandable stents manufactured by Johnson & Johnson Interventional Systems Co. of Warren, New Jersey.

The second layer 140 of balloon 126 may be united with the first layer 134 by any suitable means or methods known in the art. For instance, the first and second layers may be formed simultaneously as a multiple layer co-extrusion. Alternatively, the second layer may be sprayed, dip coated, blow molded, vacuum formed or otherwise applied to the first layer. Furthermore, in certain combinations the second layer 140 may not be especially chemically and/or physically compatible with the first layer 138. In those circumstances, the first layer 138 may be appropriately treated so as to more readily bond with the second layer 140. Perhaps most simply, the outer surface of the first layer 138 may be provided with a suitable thin (approximately 0.0001 inches thick) primer layer of an adhesive or solvent that is compatible with both the first and second layers. It will be understood that the composition of the primer layer may, of course, vary with the respective compositions of the first and second layer.

The presence of the high coefficient of friction second layer 140 although helpful in retaining the stent 28 relative to balloon 126 nevertheless has an affinity for the relatively low durometer, typically urethane, material which constitutes the tip of the guide catheter 18. As such, if balloon 126 were covered entirely with a high coefficient of friction material it would tend to stick to the guide catheter tip, thereby rendering manipulation of the stent delivery catheter rather difficult. In addition, the second layer 140 may have an affinity for itself. In other words, if provided with a self-affinitive second layer 140, when the balloon 126 is folded the folds of the balloon would tend to adhere to one another and hinder balloon expansion.

These problems may be overcome in several ways. One approach is to provide substantially the entire second layer 140, as shown in FIG. 2, with a third layer 142. Such third layer may be composed of any suitable material having a "detackifying" effect on the second layer 140 but which does not materially reduce the coefficient of friction of the second layer. Detackifier materials suitable for these purposes may include, for example, acrylonitrile copolymers such as ABS. The third layer 142 should be rather thin and desirably is no greater than about 0.0001 inches thick and may be applied using any suitable process.

Figure 3:
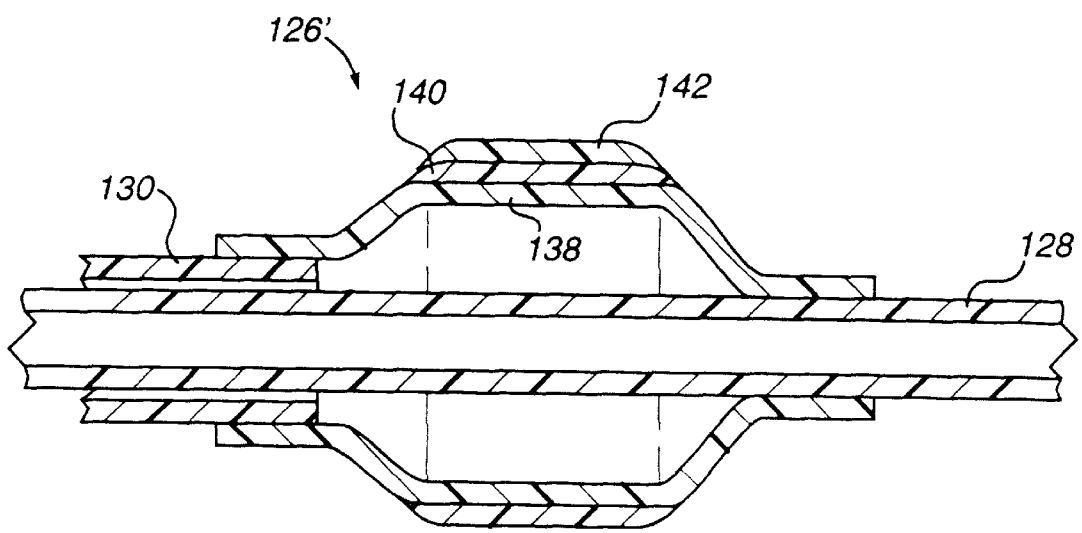
FIG. 3 is a longitudinal cross-sectional view of an inflated stent delivery balloon having stent retention means in accordance with a further preferred embodiment of the stent delivery system of the present invention.

Alternatively, as illustrated in FIG. 3, the second layer 140 may only be applied over a portion of the first layer 138, preferably over no more than the working length or central portion 136 of balloon 126'. So constructed, the third layer 142 should accordingly be provided atop the second layer 140 along the working length. Alternatively, in either of the above-described embodiments, the third layer 142 may be omitted if the material selected for the second layer 140 is sufficiently non-affinitive to itself and the guide catheter tip.

Figure 4A:
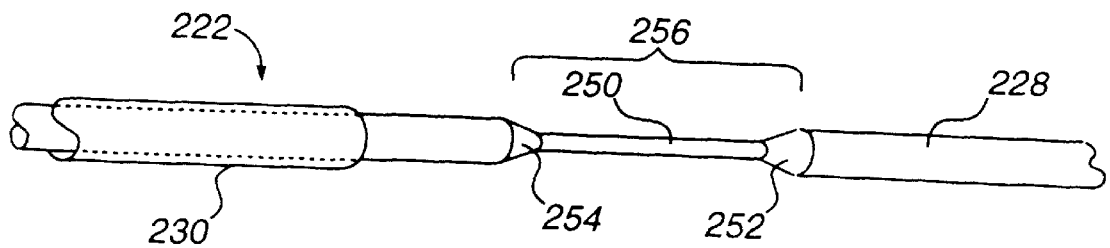
FIG. 4A is an enlarged view of the distal end of a stent delivery catheter having additional stent retention means in accordance with a further preferred embodiment of the stent delivery system of the present invention.
Figure 4B:
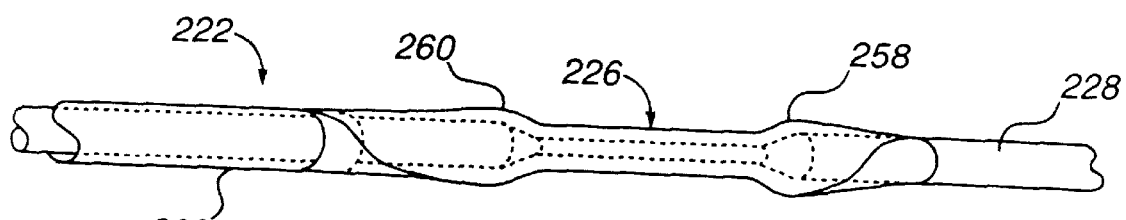
FIG. 4B is a view of the stent delivery catheter of FIG. 4A with a stent expansion balloon folded thereabout.
Figure 4C:
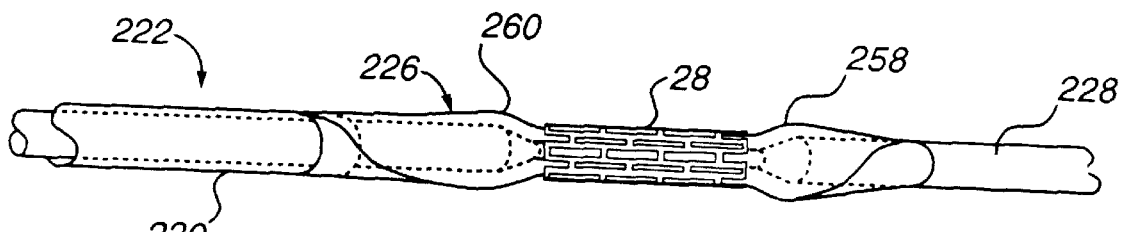
FIG. 4C is a view of the tent delivery catheter and folded stent delivery balloon of FIG. 4B with a stent crimped about the stent delivery balloon.

Referring to FIGS. 4A through 4C, there is shown a stent delivery system according to a further preferred embodiment of the present invention wherein the stent retention means additionally comprise means integral with the stent delivery catheter.

As with the above-described stent delivery catheter 22, the stent delivery catheter of FIGS. 4A through 4C, identified herein by reference numeral 222, is generally comprised of inner and outer coaxially disposed tubular body members 228 and 230, respectively, which are fabricated from flexible plastic material. Again, the annular space between the tubular members 228, 230 defines a passageway which permits injection of pressurized balloon inflation fluid into the interior of a stent dilation balloon 226 (FIGS. 4B and 4C). Moreover, the outer tubular member 230 may be constructed substantially identically to the outer tubular member 130 of stent delivery catheter 22 described above.

Inner tubular member 228, on the other hand, is preferably provided in the section thereof underlying balloon 226 with a first region of comparatively small radial dimension bounded by second regions of comparatively greater radial dimensions. According to a presently preferred embodiment, the inner tubular member 228 includes a reduced diameter portion 250 having radially outwardly projecting, and most preferably, outwardly tapered opposite ends 252 and 254. So constructed, the reduced diameter portion 250 and the relatively enlarged opposite ends 252, 254 of the stent delivery catheter inner member 222 define a recessed saddle or seat formation 256 for balloon 226.

When the balloon (which preferably has a length somewhat greater than the seat formation) is folded about the seat formation, and a stent 28 (which preferably has a length somewhat less than the seat formation as shown in FIG. 4C) is crimped about the folded balloon, the balloon generally conforms to the contours of the recessed seat formation. That is, the central portion of the balloon is compressed into the reduced diameter portion 250 of the inner tubular member 228 by the crimped stent 28. Simultaneously, the exposed opposite ends of the balloon, one of which is sealingly and fixedly attached to the inner tubular member 228 with the other being similarly attached to the outer tubular member 230, are undergirded and, therefore, urged relatively radially outwardly by the enlarged opposite ends 252, 254 of the seat formation 256. As a result, the opposite ends of the folded balloon define somewhat enlarged and generally teardrop shaped stop means 258 and 260 which further resist axial movement of the stent 28 relative to the balloon 226 during delivery and placement of the stent. Stop means 258, 260 also beneficially serve to prevent snagging of the leading and trailing edges of the stent 28 against intraluminal bodily vessel matter and provide an atraumatic transition between the catheter tip and the stent's leading edge when the distal end of the delivery catheter 222 protrudes from the surrounding guide catheter. An unillustrated but equally effective alternative construction would involve reducing the diameter of the inner tubular member 228 for a substantial portion or perhaps its entire length and providing radial protrusions of relatively larger dimensions adjacent the ends of the balloon which would spatially and functionally correspond to the enlarged opposite ends 252, 254 of the illustrated seat formation 256.

Figure 5:
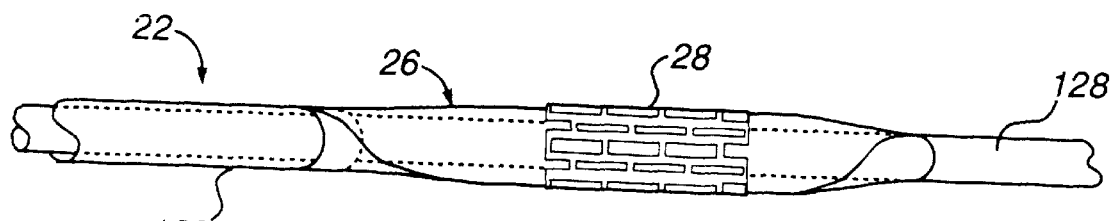
FIG. 5 is an enlarged view, sans delivery sheath, of a conventional stent delivery system.

Although enlarged relative to the reduced diameter portion 250, the opposite ends 252, 254 of the seat formation 256 (or the alternative radial protrusions) are desirably constructed so as not to exceed the radial dimensions of presently existing inner members of such catheters. Further, the tubular inner member of the present invention should be large enough to freely accommodate at least a 1 F diameter guide wire. In that way the stent delivery catheter may be used with a conventional guide wires. In addition, unlike the stent delivery catheter seat formation described in U.S. Pat. Nos. 4,733,665, 4,739,762, 4,776,337, 5,102,417 and 5,195,984 which is provided on the exterior of the catheter, the seat formation 256 is provided on the inner tubular member 228 and thus resides entirely within the profile of the outer tubular member 230. As such, the cross-sectional profile presented by the delivery catheter 222, folded balloon 226 and stent 28 is no greater than that presented by their counterpart components 22, 26 and 28 in currently available stent delivery systems such as that shown in enlarged view in FIG. 5. Likewise, it is no greater and perhaps less than the cross-sectional profiles presented by the stent delivery systems disclosed in the aforementioned U.S. patents.

The stent dilation balloon 226 of FIGS. 4B and 4C is preferably constructed so as to incorporate the features of either balloon 126 or 126' discussed above in regard to FIGS. 2 and 3. In other words, it is contemplated that the stent delivery system of the present invention may be provided with stent retention means integral with both the stent delivery catheter and the stent dilation balloon. That is, the stent retention means may incorporate both the high coefficient of friction second layer 140 provided on the dilation balloon and the stent delivery catheter inner member seat formation 256 in the same stent delivery system.

Figure 6A:
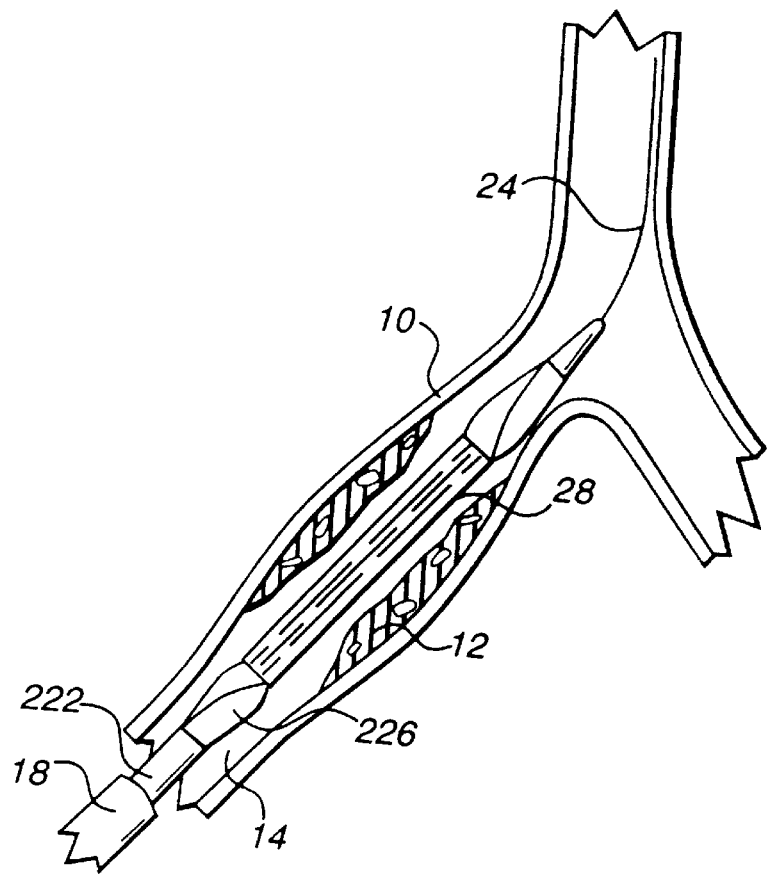
FIGS. 6A through 6C are sequential views of a stent implantation procedure using a stent delivery system constructed according to the present invention.
Figure 6B:
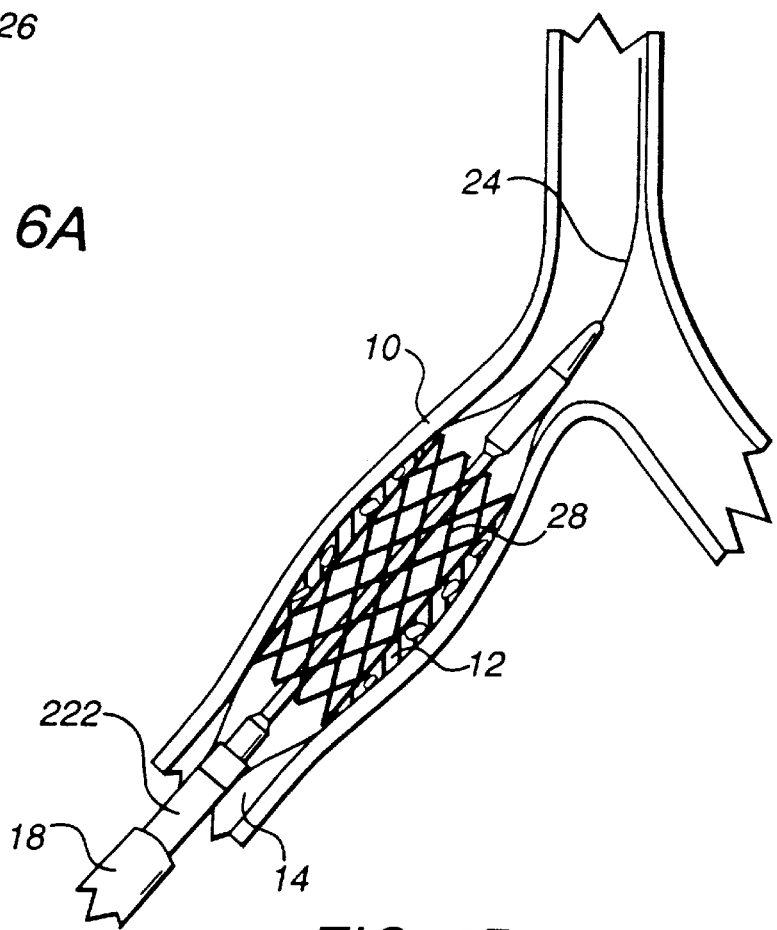
Figure 6C:
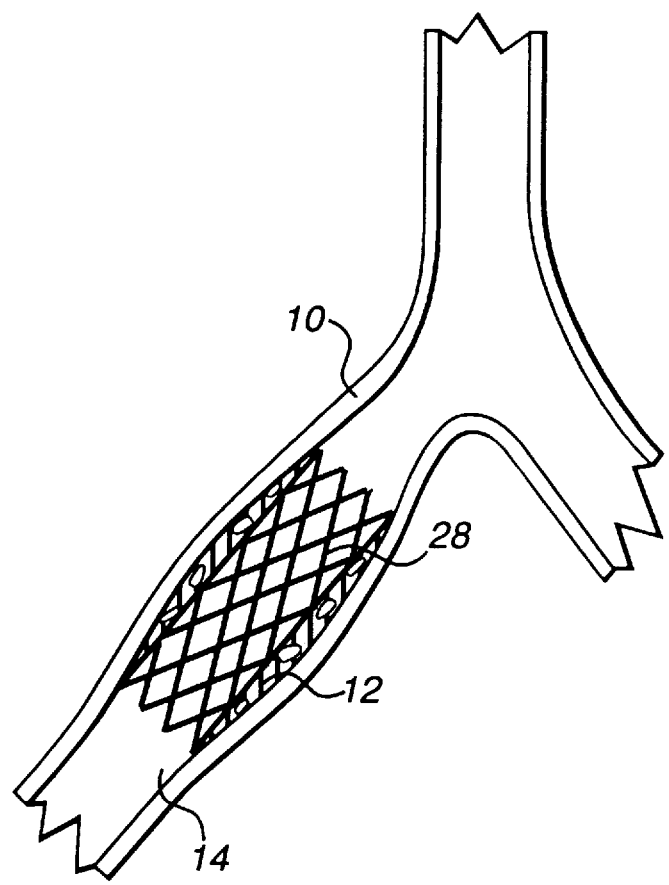

A sequential depiction of a stent implantation procedure using the stent delivery system constructed according to the present invention as manifested by the construction shown in FIG. 4C, although equally applicable to the constructions shown in FIGS. 2 and 3, is illustrated in FIGS. 6A through 6C.

As shown in FIG. 6A, following proper positioning of the guide catheter 18, the stent delivery catheter 222 is inserted into the lumen 14 of vessel 10 until the balloon 226 spans the previously dilated lesion 12. Then, referring to FIG. 6B, the balloon 226 is inflated so as to dilate and imbed the stent 28 into the vessel wall. The balloon is then deflated and the catheter is withdrawn, as reflected in FIG. 6C, leaving an open lumen 14. The stent implantation procedure is thus considerably simplified and takes less time and skill to perform as compared to that required of the conventional stent delivery system implantation process depicted in FIGS. 1B through 1E.

Furthermore, apart from enhanced stent retention, by being integral with at least the inflatable stent dilation balloon the stent retention means of the present invention eliminate the need for the delivery sheath required by may commercially available stent delivery systems. By disposing of such component, the present invention offers a stent delivery system of lesser cross-sectional profile and greater structural flexibility than heretofore achievable. As such, the present system is capable of negotiating tight lesions and tortuous anatomy with less difficulty than existing systems. It also requires a smaller introducer sheath and guide catheter and thereby reduces the possibility of bleeding complications.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A stent delivery system comprising:

a stent delivery catheter having a fluid passageway;

an inflatable stent dilation balloon having a first layer of material, said balloon being sealingly affixed to said catheter and communicating with said passageway whereby said balloon is inflatable upon introduction of a pressurized fluid into said passageway;

an expandable stent surrounding said balloon and adapted for implantation into a bodily vessel upon inflation of said balloon; and stent retention means integral with said balloon for resisting movement of said stent relative to said balloon.

2. The stent delivery system of claim 1 wherein said stent retention means comprise a second layer of material having a high coefficient of friction provided on at least a portion of said first layer.

3. The system of claim 2 wherein said second layer is selected from the group consisting of thermoplastic elastomers, rubber, latex, neoprene, and urethane compounds.

4. The system of claim 2 wherein said second layer is provided on substantially all of said first layer.

5. The system of claim 4 further comprising a third layer of material provided on at least a portion of said second layer, said third layer being operable to reduce the affinity of said second layer for itself.

6. The system of claim 5 wherein said third layer is an acrylonitrile copolymer.

7. The system of claim 1 wherein said catheter comprises coaxially disposed inner and outer tubular members defining said fluid passageway therebetween, and wherein said stent retention means further comprise means provided on said inner tubular member for defining a recessed seat formation for said balloon.

8. The system of claim 7 wherein said means for defining a recessed seat formation comprise a first region of said inner tubular member having a first radial dimension and second regions of said inner tubular member bounding said first region and having second radial dimensions greater than said first radial dimension.

9. The system of claim 8 wherein said second regions of said inner tubular member undergird said first second ends of said balloon such that said first and second ends of said balloon define stop means for resisting movement of said stent relative to said balloon.

10. The system of claim 1 wherein said catheter comprises coaxially disposed inner and outer tubular members defining said fluid passageway therebetween, and wherein said stent retention means comprise:

a second layer of material having a high coefficient of friction provided on an at least a portion of said first layer; and means provided on said inner tubular member for defining a recessed seat formation for said balloon.

11. A stent delivery system comprising:

a stent delivery catheter having a fluid passageway;

an inflatable stent dilation balloon having a first layer, said balloon being sealingly affixed to said catheter and communicating with said passageway whereby said balloon is inflatable upon introduction of a pressurized fluid into said passageway;

an expandable stent surrounding said balloon and adapted for implantation into a bodily vessel upon inflation of said balloon; and stent retention means integral with said balloon for resisting movement of said stent relative to said balloon, said stent retention means comprising a second layer of material having a high coefficient of friction provided on at least a portion of said first layer and a third layer of material provided on at least a portion of said second layer, said third layer being operable to reduce the affinity of said second layer for itself.

12. An expandable balloon for dilating and implanting a stent in a bodily vessel, said balloon comprising:

a first layer of material; and stent retention means integral with said balloon for resisting movement of a stent relative to said balloon when a stent is disposed about said balloon.

13. The balloon of claim 12 wherein said stent retention means comprise a second layer of material having a high coefficient of friction provided on at least a portion of said first layer.

14. The balloon of claim 13 wherein said second layer is selected from the group consisting of thermoplastic elastomers, rubber, latex, neoprene and urethane compounds.

15. The balloon of claim 13 wherein said second layer is provided on substantially all of said first layer.

16. The balloon of claim 13 further comprising a third layer of material provided on at least a portion of said second layer, said third layer being operable to reduce the affinity of said second layer for itself.

17. The balloon of claim 16 wherein said third layer is an acrylonitrile copolymer.

18. A stent delivery catheter for carrying an expandable balloon and a stent surrounding the balloon to a desired location within a bodily vessel, whereby expansion of the balloon dilates the stent and implants the stent in the bodily vessel, said catheter comprising:

coaxially disposed inner and outer tubular members defining a fluid passageway therebetween; and stent retention means integral with said inner tubular member for resisting movement of a stent relative to a balloon when a balloon is carried by said catheter and a stent surrounds the balloon.

19. The catheter of claim 18 wherein said stent retention means comprise means provided on said inner tubular member for defining a recessed seat formation for a balloon.

20. The catheter of claim 19 wherein said means for defining a recessed seat formation comprise a first region of said inner tubular member having a first radial dimension and second regions of said tubular member bounding said first region and having second radial dimensions greater than said first radial dimension.

21. The catheter of claim 20 wherein said second radial dimensions define the radial dimensions of said inner tubular member for substantially the entire length of said inner tubular member except for said first region.

* * * * *